United States Patent [19]
Pakker et al.

[11] Patent Number: 5,353,263
[45] Date of Patent: Oct. 4, 1994

[54] SOFT SONAR SUSPENSION SYSTEM

[76] Inventors: Ulrich Pakker, 8604 Dallas Ave. South, #4, Seattle, Wash. 98108; Dennis Feragen, P.O. Box 31505, Seattle, Wash. 98103

[21] Appl. No.: 839,774
[22] PCT Filed: Oct. 17, 1990
[86] PCT No.: PCT/US90/05954
§ 371 Date: Apr. 16, 1992
§ 102(e) Date: Apr. 16, 1992
[87] PCT Pub. No.: WO91/06192
PCT Pub. Date: May 2, 1991
[51] Int. Cl.$^5$ .............................. H04R 23/00
[52] U.S. Cl. .................... 367/173; 367/165; 181/140; 114/270; 116/27
[58] Field of Search .............. 114/270; 116/27; 367/141, 165, 173, 909; 181/140

[56] References Cited
U.S. PATENT DOCUMENTS

| | | | |
|---|---|---|---|
| 1,394,482 | 10/1921 | Fessenden | 181/125 |
| 2,407,240 | 9/1946 | Barber | 114/270 |
| 2,469,594 | 5/1949 | Danforth | 367/173 |
| 2,813,591 | 11/1957 | Smaltz et al. | 181/0.5 |
| 2,829,360 | 4/1958 | Allyn | 367/173 |
| 3,426,725 | 2/1969 | Gerhardsen | 116/27 |
| 3,740,706 | 6/1973 | Joseph | 367/173 |
| 4,144,518 | 3/1979 | Minohara et al. | 367/173 |
| 4,282,590 | 8/1981 | Wingate | 367/104 |

FOREIGN PATENT DOCUMENTS 1096255 12/1960 Fed. Rep. of Germany.
897739 5/1962 United Kingdom.

*Primary Examiner*—J. Woodrow Eldred
*Attorney, Agent, or Firm*—Christensen, O'Connor, Johnson & Kindness

[57] ABSTRACT

An underwater transducer assembly (T or P) is mounted on an elongated cylindrical piston (32 or 90) received in a pneumatic cylinder (31 or 91). One or more springs (41 or 92) normally bias the piston (32 or 90) inward into the cylinder (31 or 91) to retract the transducer assembly (T or P) into a sea chest (S'). Air under pressure introduced into the cylinder (31 or 91) is effective to overcome the force of the springs (31 or 91) and project the transducer assembly (T or P) to a position operative for scanning. Force applied to the transducer assembly (T or P) tends to move the piston (32 or 90) inward into the cylinder and thereby increase the pressure of the system. The transducer assembly (T or P) is retracted automatically if the pressure exceeds a predetermined pressure. A separate mechanical sensor is mounted adjacent to the sea chest S' to detect the presence of obstacles or debris and automatically actuate retraction of the transducer assembly (T or P).

28 Claims, 8 Drawing Sheets

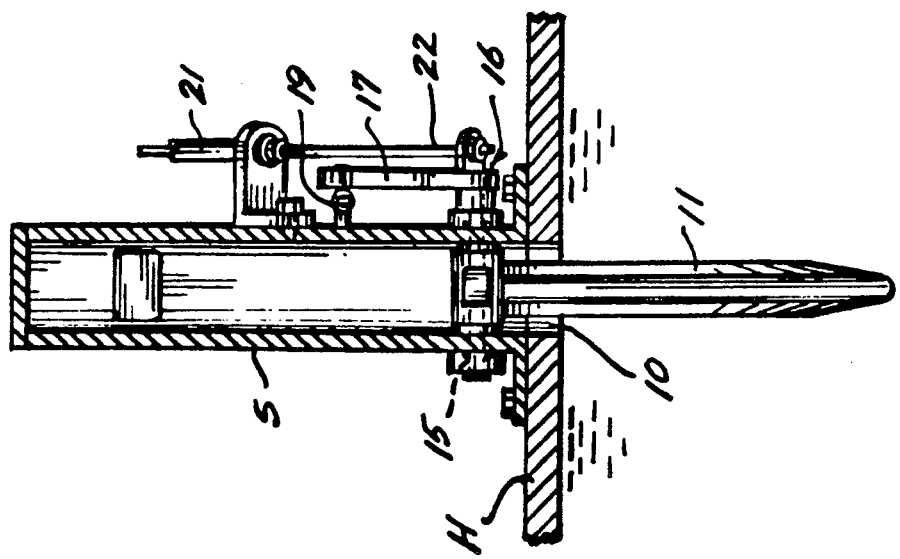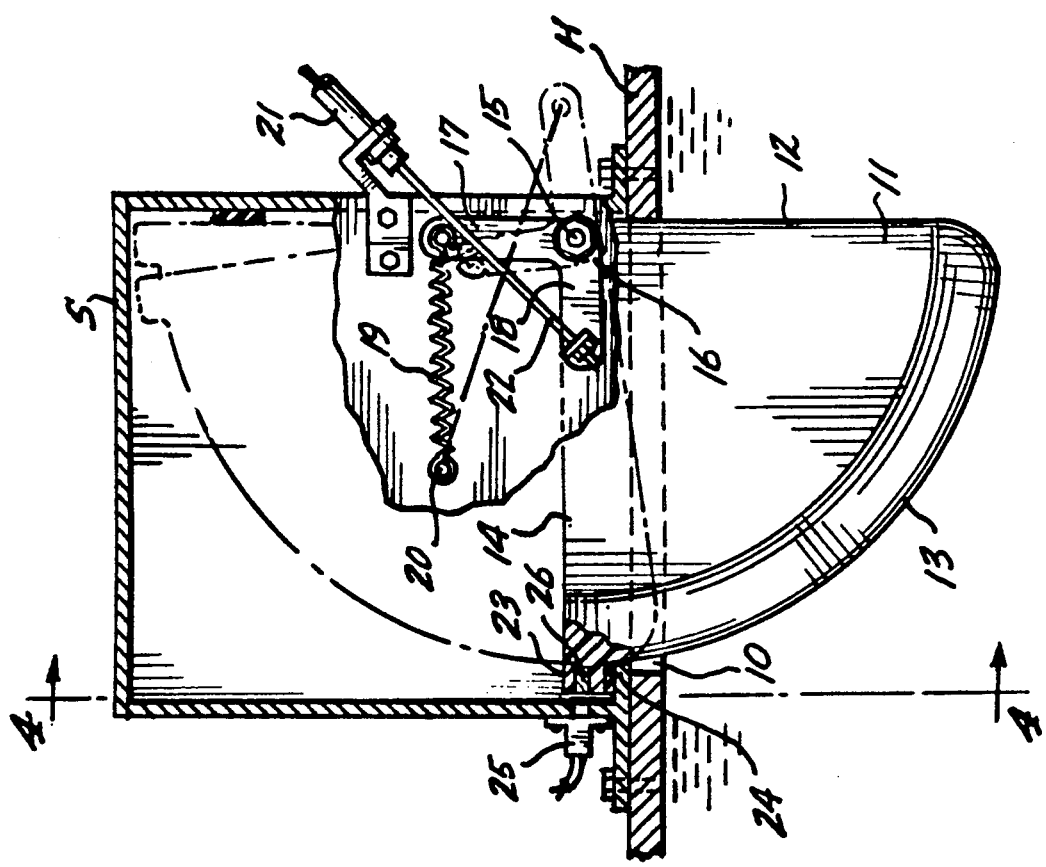

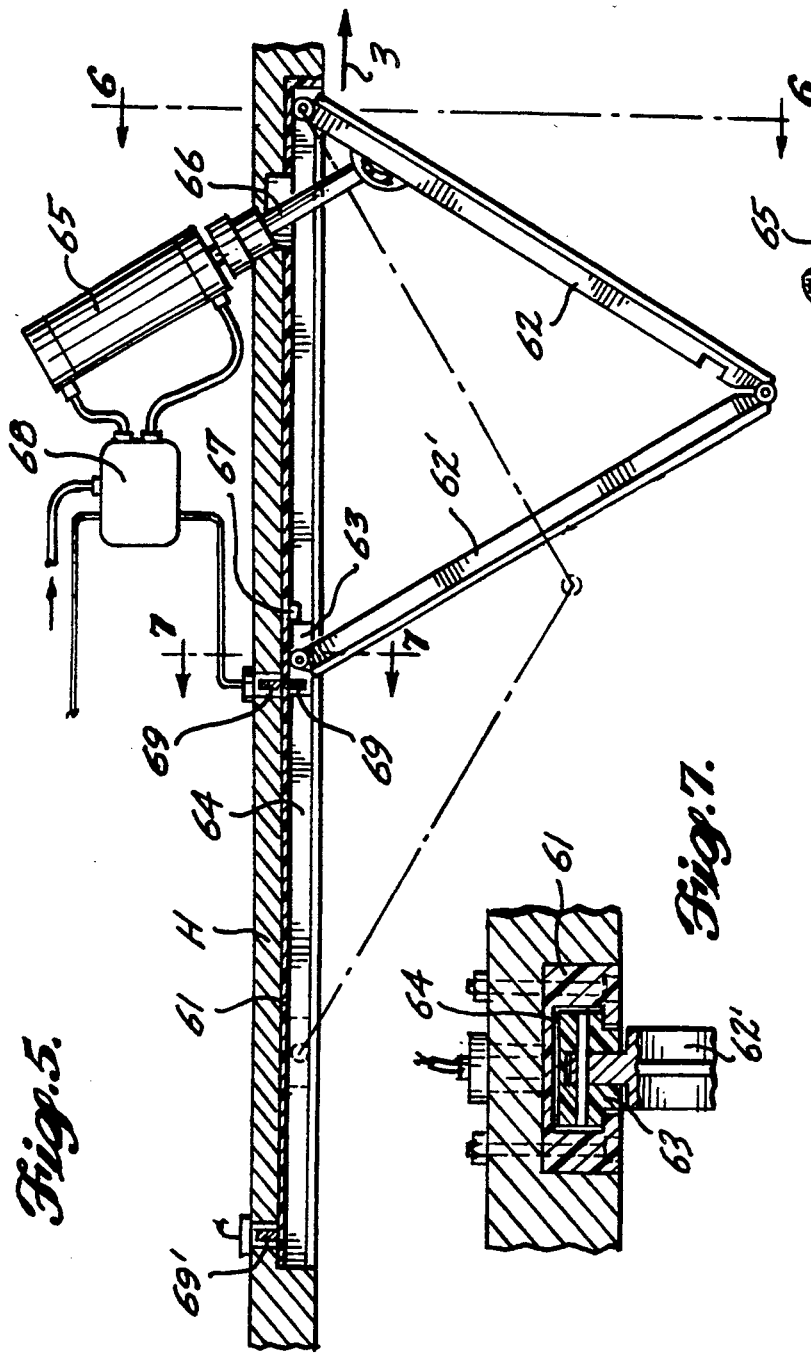

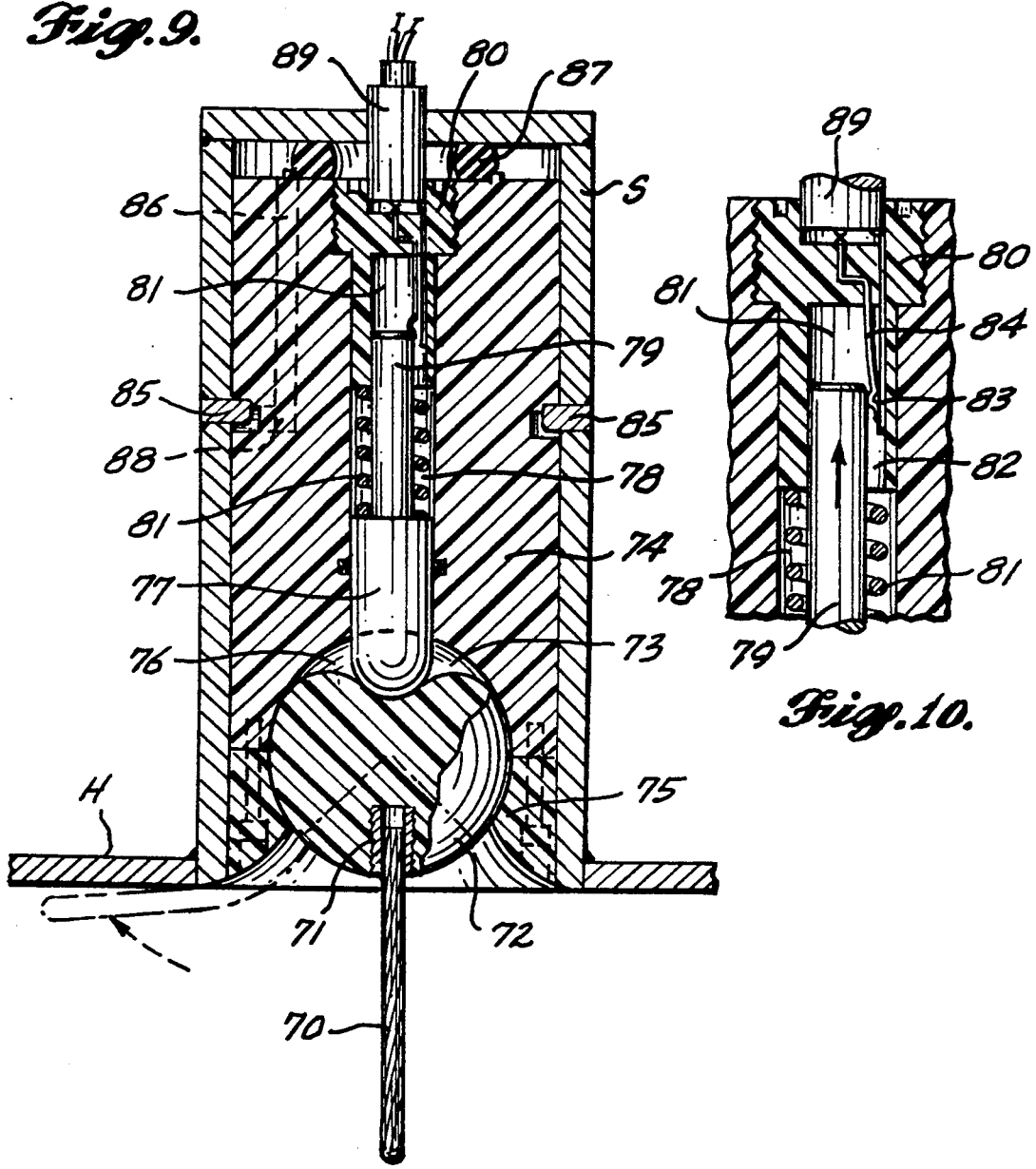

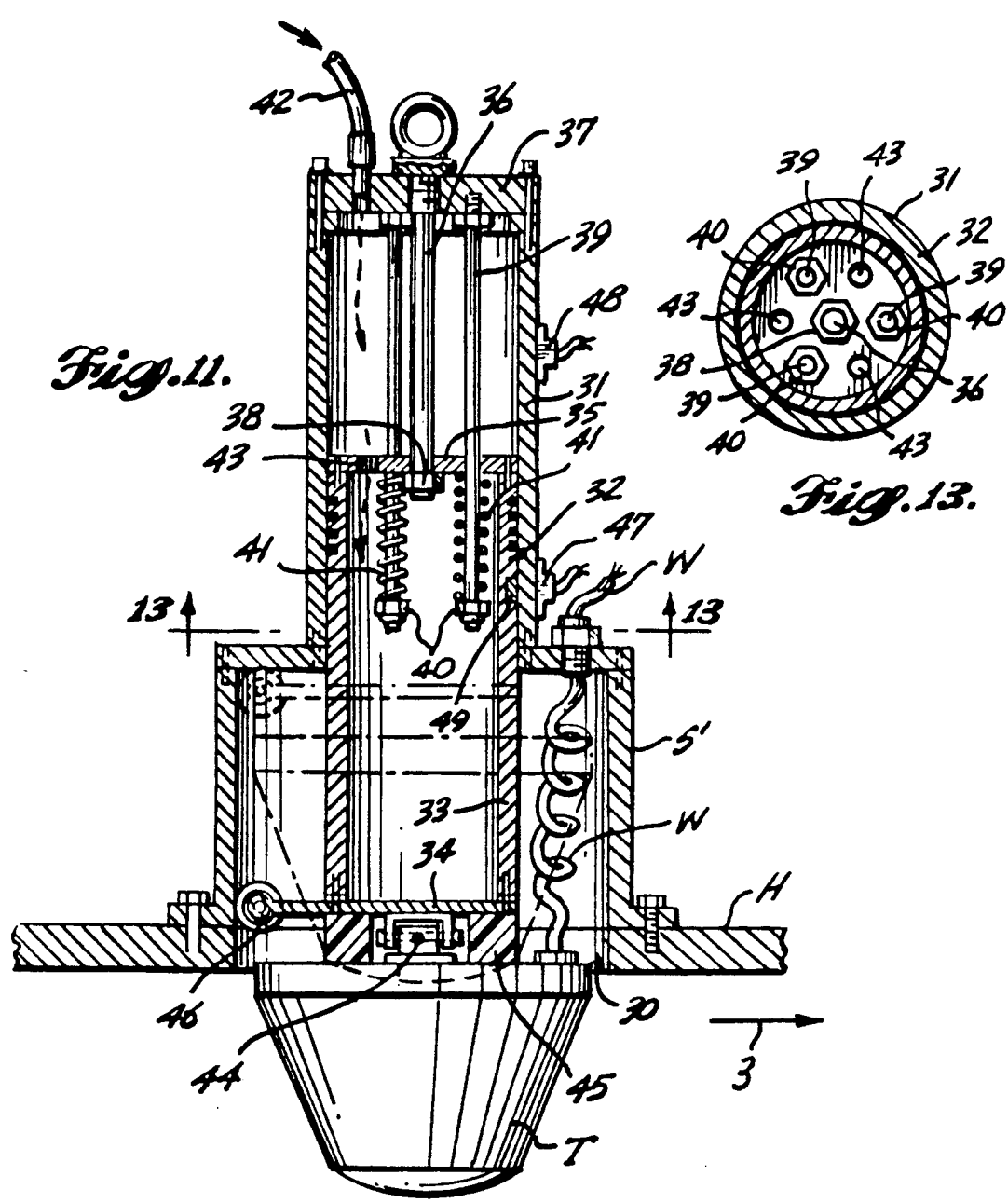

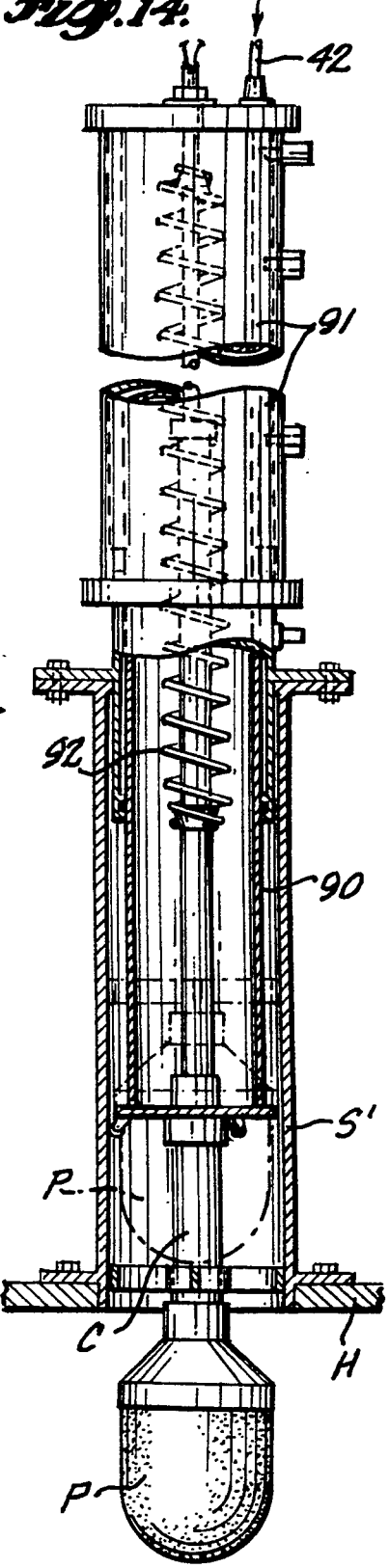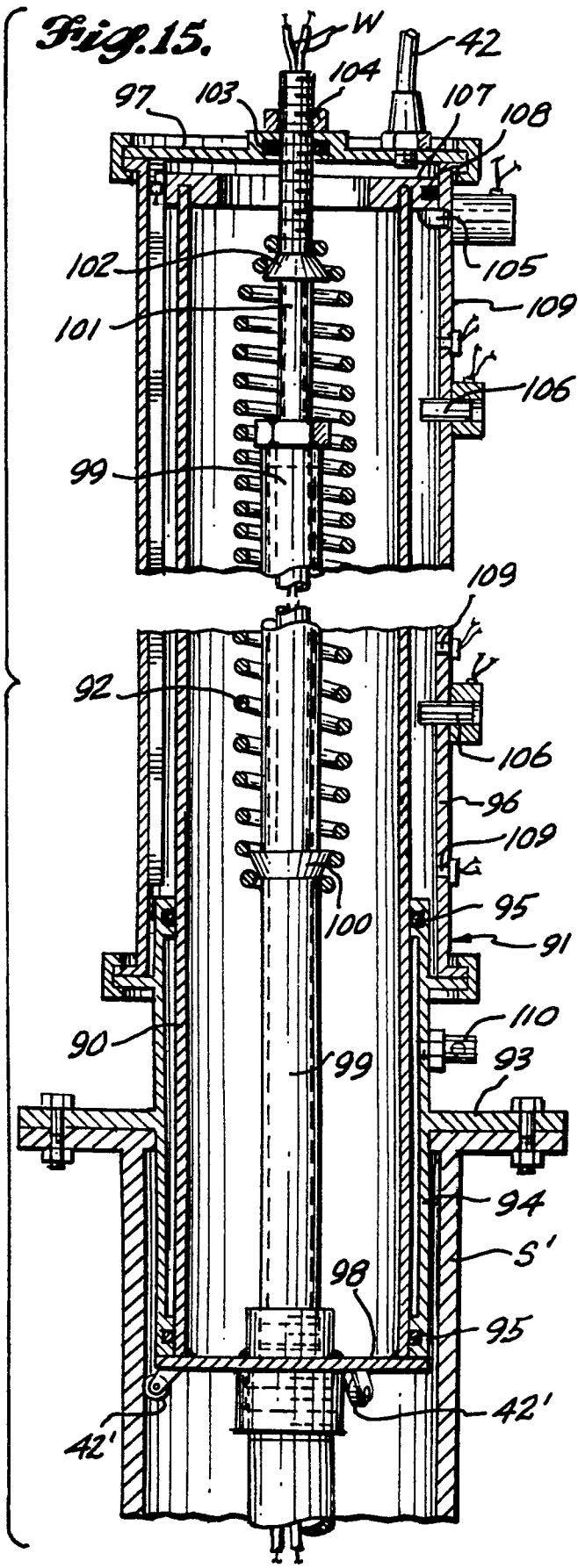

SOFT SONAR SUSPENSION SYSTEM

TECHNICAL FIELD

The present invention relates to a mount for projecting an underwater signal transducer from the hull of a marine vessel and for retracting the transducer into the hull of the vessel.

BACKGROUND ART

The devices disclosed in the following patents are representative of prior attempts to provide an in-the-hull mount for an underwater signal transducers of a marine vessel:

U.S. Pat. No. 1,394,482, issued Oct. 18, 1921 (Fessenden);
U.S. Pat. No. 2,407,240, issued Sep. 10, 1946 (Barber);
U.S. Pat. No. 2,469,594, issued May 10, 1949 (Danforth);
U.S. Pat. No. 2,813,591, issued Nov. 19, 1957 (Smaltz et al.);
U.S. Pat. No. 2,829,360, issued Apr. 1, 1958 (Allyn);
U.S. Pat. No. 3,426,725, issued Feb. 11, 1969 (Gerhardsen);
U.S. Pat. No. 4,282,590, issued Aug. 4, 1981 (Wingate);
British patent No. 897,739, dated Oct. 10, 1958 (Electroacoustic GmbH); and
Federal Republic of Germany Auslegeschrift 1 096 255, dated Dec. 29, 1960 (Electroacustic GmbH).

In each instance, the object is to provide a recessed housing or "sea chest" from which the transducer is projected. To avoid damage by collision with the bottom or debris, the transducer can be retracted into the sea chest to a position above the bottom of the hull. In the devices of the patents listed above and in equivalent in-the-hull mounts currently available, when actuated to the projected position the transducer is held in such position rigidly or substantially rigidly, such as by a rack-and-pinion or spindle drive or a hydraulic jack. The transducer and its mounting structure are vulnerable to damage if excessive force is applied. In the device disclosed in the Gerhardsen patent, the transducer is mounted in a "cup member" which can be swung to a projected position by operation of a hydraulic jack and ". . . there is provided lock means 19 for the purpose of locking the cup member in the lowermost position . . . " (column 3, lines 10–12). As explained in the paragraph beginning at column 3, line 15, > "There may also be provided an automatic supervision device, which ensures pressure supply to the device 15 if the pressure therein should fall below a certain value. Such supervision device may also be so arranged as to reduce the pressure in the device 15, to the effect that the cup member 12 may yield somewhat, in order to reduce the effects of blows against the cup, if the vessel is operating in a heavy sea."

Gerhardsen does not explain how to achieve such "yielding". In the device disclosed in that patent, the transducer assembly is held substantially rigidly in its projected position and is as vulnerable to damage by collision with the bottom or debris as the devices of the other patents listed above, particularly if struck from the rear or the side as could occur while the vessel is turning, drifting or operating in reverse.

DISCLOSURE OF THE INVENTION

The present invention provides a suspension system for a signal transducer utilizing a standard sea chest from which the transducer can be moved from a protected retracted position to an operative projected position, but with novel support structure and/or actuating mechanism for quickly and reliably retracting the transducer, preferably automatically before excessive force is applied to it. The transducer can be biased to its retracted position by springs. The force of the springs must be overcome by a pneumatic piston and cylinder combination to maintain the transducer in its projected position. The transducer assembly can be suspended from the end of the pneumatic piston. Pressure control valves can be provided so that if inward force applied to the transducer assembly increases so that pressure in the cylinder exceeds a predetermined pressure, a relief valve opens and the transducer assembly automatically retracts by the action of the springs. In addition, preferably mechanism is provided for sensing debris or an obstacle close to the boat hull adjacent to the sea chest. If debris or an obstacle is sensed, the control system for the assembly is actuated to cut off the supply of gas under pressure to the pneumatic piston and the transducer assembly will automatically retract into the sea chest.

The system in accordance with the present invention minimizes the possibility of damage to the transducer and its mounting structure if the vessel is operating in shallow water or in the area of debris or if excessive force is applied for any reason. Such system also is of simple design and inexpensive manufacture, yet durable and reliable for protecting the signal transducer over a long period of use.

BRIEF DESCRIPTION OF THE DRAWINGS

FIG. 3 is an enlarged side elevation of one component of the suspension system of FIG. 1, namely, the obstruction or debris sensor, with parts broken away, and FIG. 4 is a section along line 4—4 of FIG. 3 showing such component in rear elevation;

FIG. 5 is a side elevation of an alternative form of obstruction or debris sensor, with parts broken away, FIG. 6 is a section along 6—6 of FIG. 5, FIG. 7 is a section along 7—7 of FIG. 5, and FIG. 8 is a fragmentary side elevation of such sensor corresponding to FIG. 5, but with parts in different positions;

FIG. 9 is an a side elevation of another alternative form of obstruction or debris sensor, with parts broken away, and FIG. 10 is an enlarged fragmentary detail view of the upper portion of such sensor;

FIG. 11 is a side elevation of another component of the suspension system in accordance with the present invention, namely, the mount for the signal transducer assembly, with parts broken away, FIG. 12 is a fragmentary bottom plan of such component and FIG. 13 is a section along line 13—13 of FIG. 11;

FIG. 14 is a side elevation of an alternative mount for the signal transducer assembly, with parts broken away, and FIG. 15 is an enlarged side elevation of the upper portion of such component, with parts broken away;

BEST MODES FOR CARRYING OUT THE INVENTION

Figure 1:
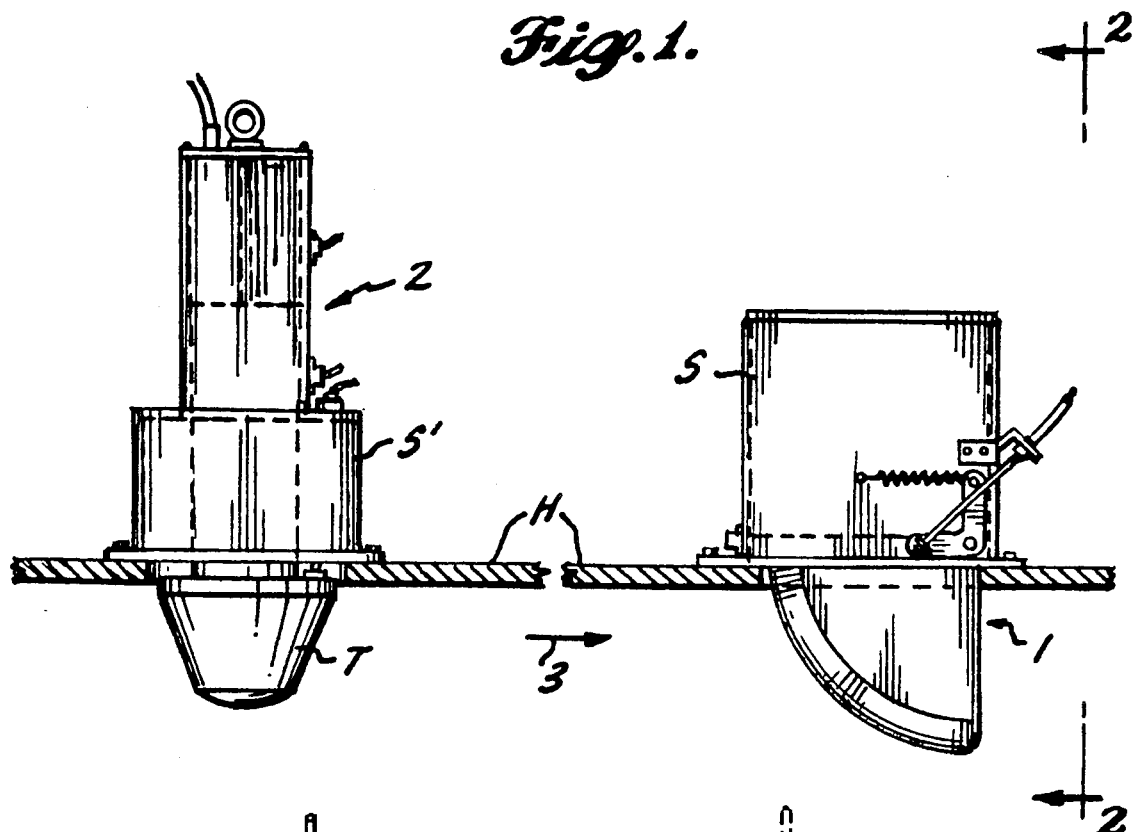
FIG. 1 is a somewhat diagrammatic side elevation of a soft sonar suspension system in accordance with the present invention with parts broken away.
Figure 2:
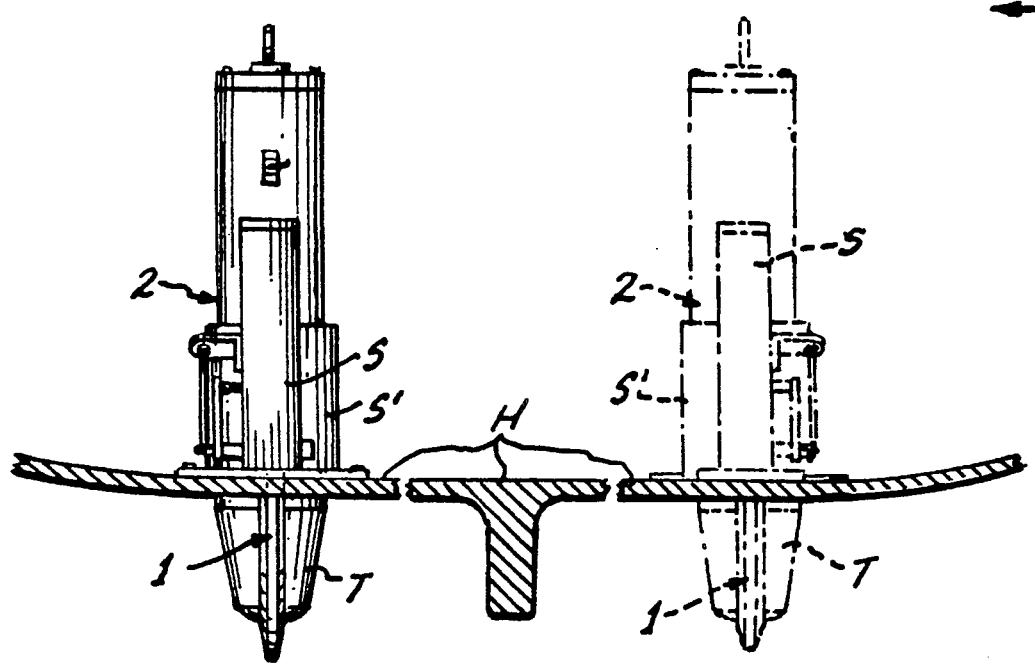
FIG. 2 is a somewhat diagrammatic front elevation of such suspension system viewed from line 2—2 of FIG. 1.

With reference to FIGS. 1 and 2, the principal components of the preferred soft sonar suspension system in accordance with the present invention are mounted in individual sea chests S and S' supported on the hull H of a marine vessel. Such components include a debris or obstacle sensing component 1 and a transducer assembly mount 2. The normal direction of forward travel of the vessel is indicated by the arrow 3 in FIG. 1.

Preferably the sensing component 1 is spaced a substantial distance forward from the transducer mount 2. Depending on the vessel and its application, a single underwater signal transducer can be provided or transducers T can be provided in pairs in side-by-side relationship at opposite sides of the centerline of the vessel as indicated in FIG. 2. In the case of multiple transducers, preferably a separate mount 2 will be provided for each of the transducer assemblies T, and a separate sensing component 1 will be provided for each transducer mount with each sensing component 1 being positioned directly in front of the corresponding mount 2.

In FIGS. 1 and 2, the transducers T are shown in their projected positions where they are operative for scanning. Each transducer mount 2 contains mechanism for retracting its transducer T to a protected position inside its sea chest S'. In addition, if an obstacle is sensed by the sensing component 1, one or both of the transducer mounts 2 is automatically actuated to retract its transducer into its sea chest without requiring any action by the operator. Further, regardless of whether or not a sensor component 1 detects the presence of an obstacle or debris, if excessive force is applied to a projected transducer assembly T, the transducer mount 2 automatically retracts such assembly without any action by the operator.

SENSOR CONSTRUCTION

With reference to FIG. 3, in a first embodiment of the invention, the sea chest S for the sensor component 1 surrounds a narrow slot 10 through the hull H. A thin, generally triangular mechanical sensing fin 11 normally projects downward through the slot 10. In its normal projected position shown in FIGS. 3 and 4, the fin has a substantially vertical leading edge 12 extending downward into the water and an arcuate trailing edge 13 curved rearward and upward back to the slot 10. In such projected position, the top edge 14 of the fin is substantially horizontal and is positioned inside the lower portion of the sea chest S.

A horizontal cross shaft 15 is fixed to the top leading corner portion of the sensor fin 11 and has its opposite ends journaled in holes through the opposite sides of the sea chest S for a pivotal mounting of the fin in the chest. At one side of the sea chest, the right side as viewed in FIG. 4, shaft 15 is fixed to the central portion of a bell crank 16 which has an upward-projecting leg 17 and a rearward-projecting leg 18 best seen in FIG. 3. A tension spring 19 has one end connected to the upper portion of the vertical bell crank leg 17 and is stretched rearward to its point of connection 20 to the sea chest for resiliently biasing the sensor fin 11 to the projected position shown in FIGS. 3 and 4. Nevertheless, the fin will swing rearward and upward into the sea chest, such as to the position shown in broken lines in FIG. 3, upon contacting an obstacle or debris when the boat is traveling in the forward direction indicated by the arrow 3. The fin also can be retracted manually by the operator of the vessel by manipulation of a Bowden cable 21 which has its actuating wire 22 connected to the rear end portion of the horizontal leg 18 of the bell crank 16.

With reference to FIG. 3, the rear end of the sensing fin 11 has a projection 23 stepped rearward from the arc of the trailing edge 13 of the fin. In the position shown in FIG. 3, such projection 23 engages against the hull or sea chest portion 24 immediately behind the slot 10 to limit downward swinging of the fin 11. Preferably, electrical sensing mechanism is provided to detect when the fin is in its downward-projected position. Such electrical sensing mechanism could be a limit switch but in the illustrated embodiment is a magnetic switch 25 which senses the close presence of a magnetic element 26 carried in the projecting portion 23 of the fin. Any substantial upward swinging of the fin 11 is detected by the switch 25 mounted on the rear upright wall of the sea chest S.

In the alternative embodiment illustrated in FIGS. 5 through 8, the sea chest is in the form of a long channel 61 recessed into the hull H of the boat. The obstacle sensor includes a pair of elongated link 62 and 62'. The leading end portion of link 62 (with reference to the forward direction of travel indicated by the arrow 3 in FIG. 5) is pivotally connected to the leading end portion of the channel 61. The trailing end portion of such link 62 is pivotally connected to the leading end portion of link 62'. The trailing end portion of link 62' is pivotally connected to a slide or carriage block 63.

As best seen in FIG. 7, the trailing portion of the channel 61 forms a T-shaped passageway 64 for the correspondingly T-shaped slide block 63. Such block is slidable rearward from the position shown in FIG. 5 in which the links 62 and 62' project from the hull of the boat to the position shown in FIG. 8 in which the links are substantially flush with the bottom of the boat hull and substantially close the bottom of the passageway of the channel 61.

As diagrammatically represented in FIG. 5, a pneumatic cylinder 65 with double-acting plunger 66 is provided for normally maintaining the links 62 and 62' in a projected position. In such position the slide block 63 engages against a stop 67 in the upper portion of the channel 61. Gas at a predetermined pressure is supplied to the jack 65 by a control system 68, illustrated diagrammatically in FIG. 5, so as to project the plunger 66. Electrical or magnetic sensing components 69 in the slide block and in or adjacent to the channel 61 detect that the sensor links 62 and 62' are projected.

If rearward directed force in excess of a predetermined force is applied to the front side of the leading link 62, the front link is forced to swing rearward, which has the effect of moving the slide block 63 rearward in its passageway 64. Such movement is detected by the change in the relative positions of the sensing elements 69. The control system 68 automatically detects such movement and actuates positive retraction of the jack plunger 66 to move the links to the retracted position shown in FIG. 8. A rear electrical or magnetic sensing component 69' can be provided to detect when the links have reached their fully retracted position. The rear end portion of the leading link 62 has a notch to receive the stop 67.

The embodiment shown in FIGS. 3 and 4 and the embodiment shown in FIGS. 5 through 8 are effective for detecting grounding of the vessel when moving in a forward direction or close proximity of an obstacle approaching the transducer mount from the front. The alternative embodiment of obstacle sensor shown in FIGS. 9 and 10 is effective for detecting an obstacle passing by the sensor in any direction. In such embodiment, the projecting sensor portion is in the form of a cable 70 of spring steel having an externally threaded fitting 71 swaged on its upper end portion. Such fitting 71 is screwed into the bottom of a general spherical ball 72 of plastic material. Such ball is mounted in a hemispherical socket 73 of a plastic cylinder 74. The ball is held in the socket by an annular bottom collar 75 bolted to the cylinder 74 and having its inner end portion shaped complementary to the ball 72 in a manner to prevent it from falling out of the hemispherical socket 73. Consequently, except for the biasing mechanism described below, from the central position illustrated in FIG. 9 in which the central sensor cable 70 extends substantially vertically, the cable and the ball in which it is mounted are free to swing a substantial distance in any direction. As indicated in broken lines in FIG. 9, excessive force applied to the cable 70 tends to bend it without structural damage to the assembly. When the force is removed, the cable springs back to its straight condition.

The upper portion of the ball 72 is rounded inward to form a central depression 76 in which the bluntly rounded lower end portion of an upright plunger 77 is normally received. Plunger 77 is fitted in a central vertical bore 78 of the cylinder 74 and has an elongated upper stem 79 of a diameter much less than the diameter of the lower portion of the plunger.

A plug 80 is fixed in the upper portion of the bore 78. The bottom of plug 80 forms a shoulder facing the shoulder formed at the bottom of the plunger stem 79. A helical compression spring 81 encircling the stem 79 between the two shoulders biases the plunger downward.

Nevertheless, by movement of the ball 72 resulting from swinging movement of the sensor cable 70 in any direction, the plunger 77 will be forced upward in its bore 78. The stem 79 of the plunger slides in a corresponding bore 81 formed in the plug 80. As best seen in FIG. 10, electrical sensing mechanism is provided for detecting upward movement of the plunger. In the embodiment illustrated, the lower portion of plug 80 has a vertical groove 82. The base of the groove has a stationary electrical contact 83. A leaf spring 84 cantilevered from the upper portion of the plug forms a second electrical contact. Upward movement of the plunger stem 79 forces the leaf spring 84 outward into contact with the stationary contact 83. Consequently, such two contacts 83 and 84 operate as a normally open switch which is closed by any substantial upward movement of the plunger resulting from engagement of the sensor 70 shown in FIG. 9 by an obstacle.

In the embodiment illustrated in FIGS. 9 and 10, the sensor unit is mounted in a cylindrical sea chest S by a bayonet latching mechanism. Latching projections 85 extend inward from the otherwise cylindrical inner periphery of the sea chest. The assembled sensor unit is insertable into the sea chest by sliding movement of such latching projections in vertical slots 86 in the outer periphery of the upper cylinder member 74 until the top of such member engages against a resilient compression ring 87. Additional upward movement of the assembly compresses the ring 87 and allows the assembly to be rotated with the projections 85 sliding in circumferential grooves 88 to latching notches in which the projections 85 are received when the assembly is released. Disassembly is reverse of the assembly for convenient removal of the sensor assembly from the sea chest, such as for servicing.

At the top of the sea chest an electrical connection plug 89 can be inserted to detect whether or not the electrical switch components are open or closed for indicating the presence or absence of an obstacle. For most efficient use, preferably an array of at least three of the sensors will be provided surrounding each of the transducer mounts.

TRANSDUCER MOUNT CONSTRUCTION

With reference to FIGS. 11 and 12, the sea chest S' for the transducer assembly T is mounted over a hole 30 through the hull H. As best seen in FIG. 12, both the hole 30 and sea chest S' are of a cross-sectional shape substantially complemental to but slightly larger than the perimeter of the transducer assembly T. In the illustrated embodiment, such assembly is elongated fore and aft for decreased resistance to forward movement through the water in the direction indicated by the arrow 3. The transducer of assembly T is powered and monitored by signals through wiring W as is conventional.

A pneumatic cylinder 31 extends upward from the horizontal top plate of the sea chest S' in alignment with the vertical axis of the sea chest and hole 30 through the hull H. A hollow cylindrical piston 32 is slidably fitted in the cylinder 31. The piston has a thin, unapertured cylindrical wall 33, of a length at least twice its diameter, a bottom plate 34 carrying the transducer assembly T and sealing the bottom of the cavity formed by wall 33 and an apertured top plate 35. A central guide and stop rod 36 extends downward from the top plate 37 which closes the top of the cylinder 31. Rod 36 extends through a central aperture of the piston top plate 35. Upward sliding movement of the piston 32 in its cylinder 31 is limited by engagement of the piston top plate 35 against the upper portion of the cylinder 31, whereas downward sliding movement of the piston 32 in its cylinder 31 is limited by engagement of the underside of its top plate 35 against a stop 38 in the form of a nut on the bottom end portion of the central rod 36.

Three additional vertical guide rods 39 extend downward from the top plate 37 of cylinder 31 through corresponding holes in the piston top plate 35. Such rods 39 are spaced equiangularly around the central rod 36 and extend inward into the piston 32 to a location much lower than the stop 38. The bottom ends of the rods 39 have enlarged heads or nuts 40. Helical compression springs 41 encircle the bottom end portions of rods 39 inside the piston and bear against such nuts and against the piston top plate 35 so as to bias the piston upward into the cylinder 31. The piston is movable downward, however, against the force of the springs 41 by introduction of air under pressure into the upper portion of the cylinder, such as through a hose 42 from a pump (not shown in FIG. 11).

In the present invention, air or another conveniently available compressed gas is used to move the piston to the projected position shown in FIG. 11 rather than a rigid mechanical actuator or a substantially rigid hydraulic actuator. Consequently, the present invention provides a softer, more resilient and yieldable biasing of the piston to its projected position which is opposed by the springs 41 exerting force in the opposite direction. Preferably, the volume of compressed gas acting on the piston to maintain it in its projected position is large for an increased cushioning effect. In this regard, the top plate 35 of the piston 32 has through apertures 43 such that the hollow interior of the piston is in communication with the upper portion of the cylinder 31. In the embodiment shown, the transducer assembly T and its sea chest S' are of generally elliptical cross section with both minor and major axes. The minimum cross-sectional dimension of the sea chest corresponds to the minor axis. The diameter of the pneumatic cylinder preferably is about the same as the minimum dimension (minor axis) of the sea chest over which it is mounted. In addition, in the projected position shown in FIG. 5, preferably the total volume of compressed gas acting on the piston, which includes the internal volume of the piston and the volume of the upper portion of the cylinder, is greater than the total volume of the sea chest. The result is a large volume of compressed gas for an increased cushioning effect without unduly increasing the height of the transducer mount.

The bottom plate 34 of the piston 32 carries a conventional universal joint 44 which, in turn, is attached to the baseplate of the transducer assembly T. Such universal joint permits limited swinging movement of the transducer assembly T relative to the piston assembly 32 in all directions. Assembly T can swing forward in the usual direction of travel of the vessel indicated by the arrow 3, rearward in the opposite direction and starboard or to port perpendicular to the usual direction of travel. The universal joint 43 is surrounded by a ring or doughnut 45 of resilient material engaged between the piston bottom plate 34 and the transducer assembly baseplate to bias the transducer assembly to a central position.

Force applied to the transducer assembly when it is projected swings it upward against the doughnut assembly so as to have an upward component tending to force the piston 32 inward into its cylinder 31. Such inward movement of the piston increases the pressure in the system and, as described further below, mechanism is provided to permit immediate and complete retraction of the piston and the transducer carried thereby upon application of excessive force. Such automatic retraction is operable regardless of the direction of application of force. Nevertheless, there is greater potential for damage by reason of rearward-directed force such as when an obstacle or debris is struck while the vessel is running. Consequently, in the preferred embodiment, the bottom plate 34 of the piston is extended rearward and carries rollers 46 engaged against or positioned immediately adjacent to the rear upright wall of the sea chest S'. The extended plate and roller construction reinforces the piston and maintains it in alignment with the bore of the cylinder 31.

As described further below, preferably mechanism is provided to indicate when the piston is projected and when it is retracted. Such mechanism can be in the form of limit switches or, as represented diagrammatically in FIG. 11, magnetic switches 47 and 48 can be mounted on the exterior of the cylinder 31. Such switches are spaced apart vertically a distance equal to the range of travel of the piston. A magnetic element 49 is embedded in the wall 33 of piston 32 at a position to be adjacent to the bottom switch 47 when the piston is fully projected as shown in solid lines in FIG. 11, whereas the magnetic element is positioned adjacent to the top switch 48 when the piston is fully retracted.

In the embodiment illustrated in FIGS. 14 and 15, the transducer assembly includes a conventional, generally cylindrical pod P and supporting conduit C mounted in the cylindrical sea chest S' secured to the boat hull H. In accordance with the present invention, conduit C is suspended from the bottom of a piston 90 slidable in an upper cylinder 91. A tension spring 92 normally biases the piston to its upper position in which the pod P is retracted into the sea chest, as illustrated in broken lines in FIG. 14. When it is desired to project the pod, air is injected into the upper portion of the cylinder, such as through the tube 42, so as to force the piston 90 downward.

As shown in more detail in FIG. 15, the upper cylinder 90 includes a bottom portion 93 bolted to the top of the sea chest S'. The cylindrical upright wall 94 of such cylinder portion 93 extends partway into the sea chest. Seals 95 are provided at the top and bottom of such portion. A vent 110 can be provided between the seals. An upper cylinder portion 96 is secured to the bottom portion 93 in airtight relationship. The top of such upper stationary cylinder portion 96 is closed by a top plate 97.

In the retracted position of the piston 90 illustrated in FIG. 15, its bottom plate 98 engages against the bottom of the lower cylinder portion 93. An inner conduit 99 extends upward from the piston bottom plate and carries a spring retainer 100 intermediate the top and bottom ends of such inner conduit. An upper conduit 101 is telescoped inside conduit 99 in substantially airtight condition and carries a top spring retainer 102. Tension spring 92 extends between such two spring retainers for biasing the piston to the retracted position shown in FIG. 15.

Whereas inner conduit 99 moves with the piston, the upper conduit 101 is stationary relative to the cylinder 91. More specifically, the upper end portion of the inner conduit extends through a seal 103 in the cylinder top plate 97. Such upper portion has external threads for a nut 104 allowing the tension of the spring 92 to be adjusted by turning the nut. Wiring W for the transducer assembly extends through the upper conduit 101, inner conduit 99, piston bottom plate 98 and conduit C to the transducer pod P.

In the embodiment shown in FIGS. 14 and 15, a solenoid operated latch mechanism 105 can be provided to lock the piston in its upper position until it is actuated to be projected. In addition, different projected positions of the piston can be selected. Small solenoid actuated stops 106 are provided along the length of the cylinder 91 and, by remote control, can be projected inward into the path of an annular stop ring 107 carried at the top of the piston 90. For example, with all of the intermediate stop pins 106 retracted into the wall of the cylinder 91, introduction of air under pressure through the tube 93 will force the piston downward until the stop ring 107 engages against the top of the bottom cylinder portion 93. If, however, one of the solenoid actuated stop pins 106 is actuated to project inward, the piston will stop when its stop ring 107 engages such pin. Rollers 42' can be carried by the piston bottom plate to roll along the inner periphery of the sea chest and center the piston in the chest. In the illustrated embodiment, three such rollers are provided spaced equiangularly around the circumference of the piston.

Preferably, electrical sensing mechanism is provided to indicate when the piston is in its upper retracted or lower projected position. For example, a magnet 108 can be carried by the stop ring 107 to be registered with the appropriate magnetic reed switch 109 adjacent to the selected stopping point.

Figure 16:
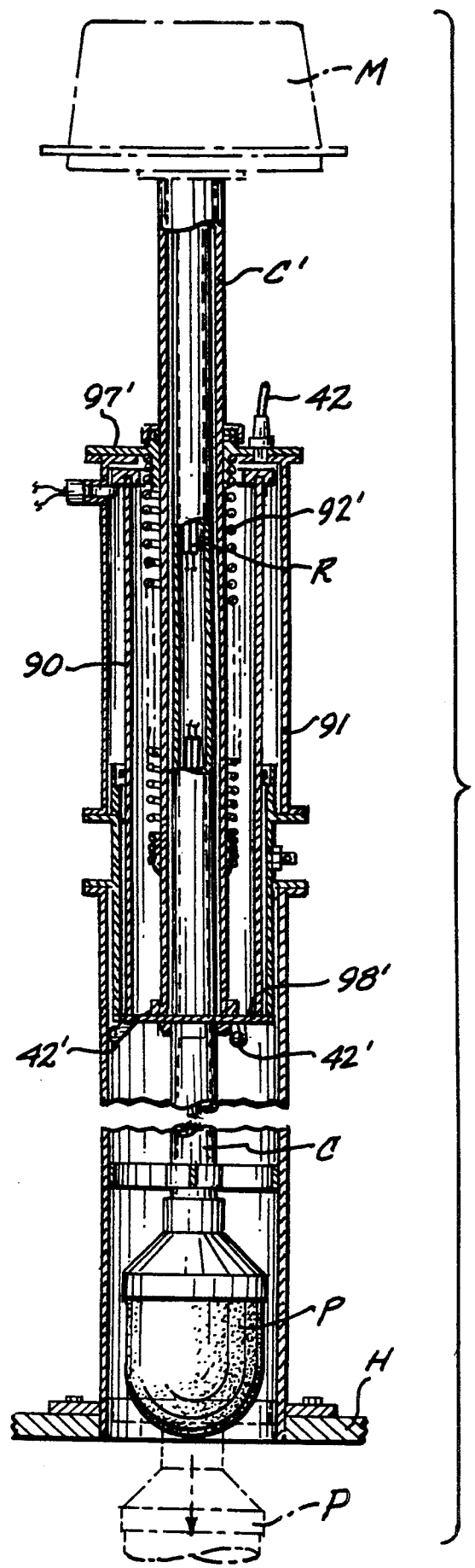
FIG. 16 is a side elevation of another embodiment of a mount for the signal transducer assembly, with parts broken away.

The embodiment illustrated in FIG. 16 is very similar to the embodiment shown in FIGS. 14 and 15 except that it has been modified to be used with the type of system having a "tilt and train" motor M for controlling the position of a transducer within the pod P. Such motor is mounted on a conduit C' extending through the top plate 97' of the cylinder 91. The construction of cylinder 91 is otherwise essentially the same as the construction of the cylinder for the embodiment shown in FIGS. 14 and 15. Conduit C' extends downward all the way to the bottom plate 98' of the piston 90. Seals in the cylinder top plate 97' prevent escape of gas under pressure introduced through the hose 93. A tension spring 92' has one end portion secured to the top plate 97' and the other end portion secured to the conduit C' inside the piston. Such tension spring biases the conduit C' and, consequently, motor M to the retracted position illustrated in solid lines in FIG. 16. A control rod R extends through the conduit C' and conduit C to the transducer assembly in pod P for controlling the position of the transducer within the pod as is conventional.

OPERATION

Figure 17:
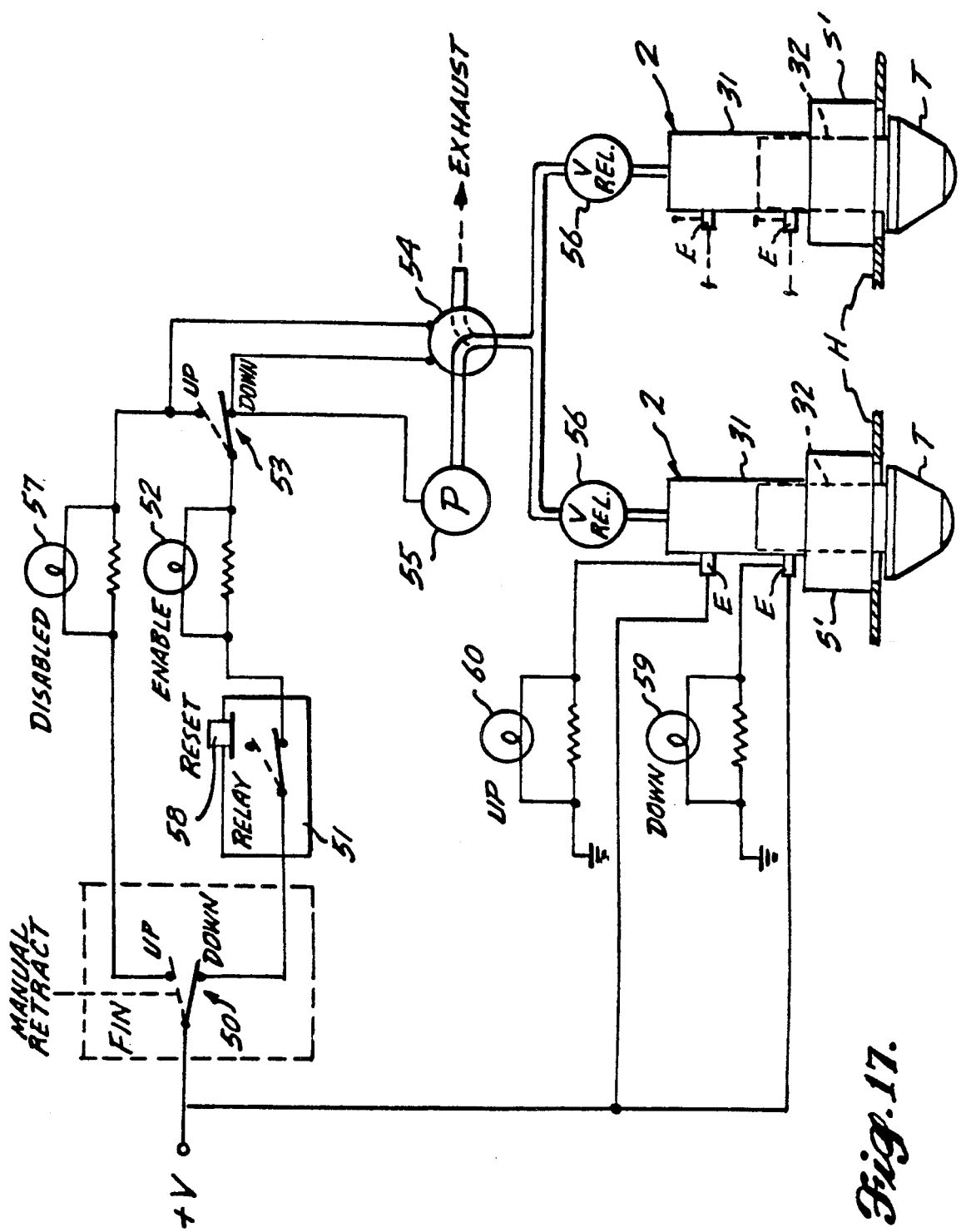
FIG. 17 is a schematic diagram illustrating the operation of a soft sonar suspension system in accordance with the present invention.

FIG. 17 is a schematic diagram for the purpose of illustrating the operation of the control system of the present invention. The obstacle and debris sensing component is represented as a switch 50 having up (retracted or vertical) and down (projected or swung) positions. With the component fully projected, electrical power is supplied through the switch to actuate a relay 51 to the solid line condition shown in FIG. 17. On a control panel, an "enable" indicator light 52 is lit to confirm that power is supplied to a manual control switch 53. Such control switch can be manipulated to actuate a solenoid valve 54 which receives compressed gas under pressure from any convenient source such as a pump 55. In the representation of FIG. 17, moving the control switch 53 to its down position supplies power to the pump 55 and also actuates the solenoid valve to the condition shown in solid lines where compressed gas is supplied to the transducer mounts 2 so as to project the transducer assemblies T from the hull H of the vessel.

If excessive force is applied to either transducer assembly T, the piston 32 (or 90) is forced into its cylinder 31 (or 91), the pressure of the system increases and a relief valve 56 is opened automatically such that both transducers retract by the action of the springs previously described. Preferably, the relief valves 56 are of the type which close automatically when excess pressure no longer is present in the system.

The manual control switch also can be used to retract the transducer assemblies T. When moved to the broken line "up" position shown in FIG. 17, power to the pump is cut off and the solenoid valve 54 is actuated to the broken line position where gas under pressure is exhausted from the mounts 2 so that the transducer assemblies T will automatically spring-retract.

Actuation of the obstacle sensor switch 50, such as by upward swinging due to contact with an obstacle or debris, has the effect of moving switch 50 to its broken line "up" position. Power to the relay 51 is cut off which automatically opens the relay switch and cuts off the supply of power to the "enable" indicator light 52 and manual control switch 53. Instead, power is supplied through a "disabled" indicator light 57 and directly to the solenoid valve 54 causing it to move to its broken line position in which air from the transducer mounts 2 is exhausted for automatic spring-retract of the transducers. When the obstacle or debris passes, the sensor is returned to its projected position but, preferably, relay 51 must be manually reset such as by a button 58 in order to supply power through the relay to the manual control switch 53.

Operation of the system can be monitored by the indicator lights. As noted above, light 52 indicates an "enable" condition in which the position of the transducer assemblies T can be controlled by manipulation of the manual control switch 53. Illumination of indicator light 58 indicates that the system is "disabled" by reason of sensing of an obstacle or debris by retraction of the sensor fin. Preferably, the control panel includes at least two other lights for each transducer mount, namely, a "down" indicator light 59 controlled by the corresponding magnetic switch 47 to indicate that the associated transducer assembly is projected, and an "up" indicator light 60 controlled by magnetic switch 48 to indicate that the associated transducer assembly is retracted.

The electrical sensors 47 which detect the positions of the transducer assemblies T also can actuate automatic retraction of such assemblies. If sufficient force is applied to a transducer assembly to move it inward above its fully retracted position, the control system can be designed to trip the relay 51 automatically and actuate valve 54 to its "exhaust" position. The operator will be alerted to excessive force having been applied to one or both of the transducer assemblies and, preferably, manual action will be required to "enable" the system for projecting the assemblies, such as manually resetting the relay.

We claim:

1. In an in-the-hull mount for an underwater transducer assembly including a sea chest and means for moving the assembly between a protected position retracted into the sea chest and an operative position projected from the sea chest, the improvement comprising the moving means including retraction means for normally biasing the transducer assembly to its protected position, a source of fluid under pressure, and projection means operable by fluid from said source to act against and overcome the force of the retraction means so as to move the assembly to its operative position.

2. In the mount defined in claim 1, the retraction means including a spring constantly exerting a force tending to move the transducer assembly to its protected position.

3. In the mount defined in claim 1, the projection means including a fluid pressure cylinder and a piston received in said cylinder, the transducer assembly being mounted on said piston such that force applied to the transducer assembly tends to move said piston inward into said cylinder so as to increase the pressure of fluid in said cylinder, and including a pressure relief valve connected to said cylinder for exhausting fluid under pressure therefrom when the pressure of fluid in said cylinder exceeds a predetermined pressure.

4. In the mount defined in claim 1, the source supplying gas under pressure, and the projection means including a pneumatic cylinder and a piston received in said cylinder and carrying the transducer assembly.

5. In the mount defined in claim 4, and means for automatically exhausting gas from the pneumatic cylinder when pressure above a predetermined pressure is present in such cylinder so that the transducer assembly is automatically moved to its protected position by the retraction means.

6. In the mount defined in claim 1, the projection means including a fluid pressure cylinder and a piston mounted in said cylinder and carrying the transducer assembly, the transducer assembly being mounted on said piston such that force exerted on said assembly tends to move said piston inward into said cylinder, and including means for detecting inward movement of said piston caused by force exerted against the transducer assembly and for automatically exhausting gas from said cylinder when inward movement in excess of a predetermined movement is detected so that the transducer assembly automatically retracts to its protected position by the action of the retraction means.

7. In the mount defined in claim 1, and means separate from the moving means and the transducer assembly for sensing the presence of an obstacle or debris adjacent to the sea chest and for automatically actuating the moving means to retract the transducer assembly to its protected position when an obstacle or debris is sensed.

8. In the mount defined in claim 7, the sensing means including a mechanical sensor mounted in the hull and movable by engagement against an obstacle or debris and means for sensing movement of said mechanical sensor.

9. In the mount defined in claim 1, the projection means including a fluid pressure cylinder and a piston received in said cylinder, and including a universal joint mounting the transducer assembly on said piston and permitting limited resilient swinging movement of the transducer assembly relative to said piston in all directions such that force applied to the transducer assembly tends to swing the transducer assembly relative to said piston and exert a force tending to move said piston inward into said cylinder.

10. In the mount defined in claim 1, the projection means including a fluid pressure cylinder and a piston received in said cylinder, the cross-sectional size of said piston being smaller than the maximum cross-sectional size of the transducer assembly, and including a reinforcement member projecting from said piston and having a roller for engagement in the cavity of the sea chest.

11. In the mount defined in claim 1, the projection means including a fluid pressure cylinder and a piston received in said cylinder, said piston being elongated axially of said cylinder and having an internal cavity in open communication with the interior of said cylinder.

12. In the mount defined in claim 11, the cylinder being a pneumatic cylinder actuated by gas under pressure from the source.

13. In the mount defined in claim 11, the retraction means including a rod projecting into the cavity of the piston and a helical spring encircling the portion of said rod received in the piston.

14. In the mount defined in claim 1, the improvement further comprising electrical sensors for detecting when the transducer assembly is in its protected and operative positions, respectively.

15. In the mount defined in claim 14, the electrical sensors including switches mounted adjacent to the sea chest and spaced apart a distance approximately equal to the range of motion of the transducer assembly between its protected and operative positions and means moved with the transducer assembly for actuating said switches.

16. In an in-the-hull mount for an underwater transducer assembly including a sea chest and means for moving the assembly between a protected position retracted into the sea chest and an operative position projecting from the sea chest, the improvement comprising the moving means including a pneumatic cylinder, a piston received in said cylinder and carrying the transducer assembly, and means for automatically retracting the transducer assembly when pressure in the pneumatic cylinder exceeds a predetermined pressure, the retracting means including spring means normally biasing the transducer assembly to its protected position.

17. In the mount defined in claim 16, the retracting means including a pressure relief valve actuated when pressure in the pneumatic cylinder exceeds the predetermined pressure to exhaust gas from the cylinder.

18. In an in-the-hull mount for an underwater transducer assembly including a sea chest and means for moving the assembly between a protected position retracted into the sea chest and an operative position projecting from the sea chest, the improvement comprising an obstacle sensor for detecting the presence of debris adjacent to the sea chest, and control means actuated by said sensor to retract the transducer assembly automatically to its protected position when debris is sensed by said obstacle sensor.

19. In the mount defined in claim 18, the obstacle sensor including a mechanical member normally projected from the hull but automatically moved by engagement against debris and means for sensing movement of said member.

20. In the mount defined in claim 19, the improvement further comprising a housing for receiving a portion of the mechanical member, the sensing means including a first magnetic element carried by the mechanical member, a second magnetic element carried by said housing and means for detecting relative movement of said two magnetic members and for triggering retraction of the transducer assembly.

21. In the mount defined in claim 19, the improvement further comprising a housing for receiving a portion of the mechanical member, the sensing means including a first electrical switch component carried by the mechanical member, a second electrical switch component carried by said housing and means for detecting relative movement of said two electrical switch components and for triggering retraction of the transducer assembly.

22. In the mount defined in claim 19, the improvement further comprising the portion of the mechanical member normally projected from the hull being resilient.

23. In the mount defined in claim 19, the improvement further comprising the portion of the mechanical member normally projected from the hull being a resilient cable.

24. In the mount defined in claim 19, the improvement further comprising a housing for receiving a portion of the mechanical member, said housing including a socket, the mechanical member including a ball received in said socket for universal swiveling movement relative thereto.

25. In the mount defined in claim 24, the improvement further comprising means for biasing the ball to a predetermined position relative to the socket, the mechanical member including a portion projected from the hull when the ball is in such predetermined position.

26. In the mount defined in claim 25, the improvement further comprising the means for biasing the ball to the selected position including a spring loaded plunger having a portion engaged against the ball.

27. In the mount defined in claim 26, the improvement further comprising the ball having a depression adjacent to the spring loaded plunger, and the plunger having a portion received in said depression when the ball is in the predetermined position such that swiveling movement of the ball moves the plunger relative to the housing.

28. In the mount defined in claim 26, the improvement further comprising means for detecting movement of the plunger within the housing and for triggering retraction of the transducer assembly.

* * * * *

UNITED STATES PATENT AND TRADEMARK OFFICE
CERTIFICATE OF CORRECTION

PATENT NO. : 5,353,263
DATED : October 4, 1994
INVENTOR(S) : Pakker et al.

It is certified that error appears in the above-identified patent and that said Letters Patent is hereby corrected as shown below:

COLUMN     LINE

1              Below Title   Following the title, insert
                             --Cross-Reference
                                This application is a continuation-in-part of application Serial No. 07/422,835, filed on October 17, 1989, titled "SOFT SONAR SUSPENSION SYSTEM", now abandoned.--

Signed and Sealed this

Seventh Day of February, 1995

Attest:

BRUCE LEHMAN

Attesting Officer    Commissioner of Patents and Trademarks